United States Patent [19]

Lampson et al.

[11] Patent Number: 5,079,151
[45] Date of Patent: Jan. 7, 1992

[54] PRODUCTION OF BRANCHED RNA-LINKED MULTI-COPY SINGLE-STRANDED DNA USING PERMEABILIZED CELLS

[75] Inventors: Bert C. Lampson, Highland Park; Masayori Inouye; Sumiko Inouye, both of Bridgewater, all of N.J.

[73] Assignee: University of Medicine and Dentistry of New Jersey, Newark, N.J.

[21] Appl. No.: 315,427

[22] Filed: Feb. 24, 1989

[51] Int. Cl.$^5$ .................. C12P 19/34; C07H 21/00; C12N 9/00
[52] U.S. Cl. ........................ 435/91; 536/27; 435/183; 435/822
[58] Field of Search .............. 435/91, 89, 822; 935/2, 935/3, 6, 16, 17

[56] References Cited

PUBLICATIONS

Hsu, M. Y. et al. 1989, *J. Biol. Chem.* vol. 264, pp. 6214–6219.
Lim, D. et al. 1989, *Cell* vol. 56 pp. 891–904.
ATCC Catalogue of Bacteria & Bacteriophages 17th edition 1989, American Type Culture Collection, p. 149.
Moses, R. E. et al. 1970, Proc. Nat. Acad. Sci. U.S.A., vol. 67 pp. 674–681.
Peterson, R. L. et al. 1971, J. Bacteriol. vol. 107 pp. 585–588.
Geider, K. et al. 1971, Eur. J. Biochem. vol. 21, pp. 374–384.
Hilderman, R. H. et al. 1976, Archiv. Biochem. Biophys. vol. 175, pp. 534–540.
Dhundale, A., et al. 1987, Coll, vol. 51 pp. 1105–1112.
Moses, R. E., et al. 1971, Chemical Abstracts, vol. 74, Abstract 29189.
Peterson, R. L., et al. 1971, Chemical Abstracts, vol. 75, abstract 72923.
Geider, K., et al. 1971, Chemical Abstracts, vol. 75, abstract 126881.
Deutscher, M. P., et al. 1974, Chemical Abstracts, vol. 81, abstract 10596.
Hilderman, R. H., et al. 1976, Chemical Abstracts, vol. 85, abstract 75812.
Furuichi, et al., "Branched RNA Covalently Linked to the 5' End of a Single-Stranded DNA in *Stigmatella aurantiaca*: Structure of msDNA", *Cell*, 48, 47–53 (1987).
Furuichi, et al., "Biosynthesis and Structure of Stable Branched RNA Covalently Linked to the 5' End of Multicopy Single-Stranded DNA of *Stigmatella aurantiaca*", *Cell*, 48, 55–62 (1987).

Primary Examiner—Richard A. Schwartz
Assistant Examiner—Mary E. Mosher
Attorney, Agent, or Firm—Weiser & Stapler

[57] ABSTRACT msDNA is a peculiar molecule consisting of a branched RNA linked to single-stranded DNA via a 2', 5' phosphodiester bond. A cell-free system, utilizing cells permeablized with phenethyl, alcohol, was established to study the synthesis of msDNA in *Myxococcus xanthus*. Permeablized cell labeled with [$\alpha$-$^{32}$P]dCTP in the presence of ddGTP, ddATP, or ddTTP, produce a band that migrates at the same position as the full-sized msDNA in an acrylamide gel. However, when this band is treated with ribonuclease A prior to gel electrophoresis, it resulted in many bands of different sizes. This indicates that during the labeling, intermediates are produced in which single-stranded DNAs of various lengths are associated with a compensatory length of RNA such that the total length for each intermediate is identical. These results provide evidence for the previously proposed model in which msDNA is synthesized by reverse transcriptase using a folded RNA precursor as a primer as well as a template. Furthermore, it was found that there is a precise coupling mechanism of reverse transcriptase and ribonuclease H.

17 Claims, 5 Drawing Sheets

PRODUCTION OF BRANCHED RNA-LINKED MULTI-COPY SINGLE-STRANDED DNA USING PERMEABILIZED CELLS

CROSS REFERENCE TO RELATED APPLICATIONS

This patent application is related to two patent applications co-filed on Feb. 24, 1989 identified as REVERSE TRANSCRIPTASE FROM *MYXOBACTERIA*, Inouye et al, having Ser. No. 07/315,316 REVERSE TRANSCRIPTASE FROM *ESCHERICHIA COLI*, Lampson et al. having Ser. No. 07/315,432.

BACKGROUND OF THE INVENTION

An extrachromosomal DNA molecule of unknown function, designated multicopy single-stranded DNA or msDNA, is of keen interest for its unusual structural features. Occurring at about 700 copies per genome, msDNA was first discovered in the soil bacterium *Myxococcus xanthus* (Yee et al., 1984). *M. xanthus*, a myxobacterium, is a Gram-negative rod which, upon starvation, aggregates into a multicellular state followed by a complex morphogensis into a fruiting body containing spores ( Kaiser, 1986; Shimkets, 1987). In addition to several other diverse species of myxobacteria which also contain msDNA (Dhundale et al., 1985), msDNA has recently been found in a clinical isolate of *Escherichia coli* (Lampson et al., 1989).

Nucleotide sequencing of msDNA from *M. xanthus* (msDNA-Mx162) revealed that the molecule is composed of a single-strand of DNA of 162 bases, and attached to the 5' end is a unique, branched RNA molecule of 77 nucleotides. The single-stranded RNA (msRNA) is linked to the 5' end of the DNA strand at the 20th granosine residue via a unique 2', 5' phosphodiester bond (Dhundale et at., 1987).

A nearly identical molecule has been characterized from another myxobacterium *Stigmatella aurantiaca* (Furuichi et al., 1987a,b). In addition, a smaller species of msDNA (designated msDNA-Mx65), which coexists in *M. xanthus*, also shares the same key structural features with the larger msDNA including a branched rG residue, a DNA-RNA hybrid at the 3' ends of the msDNA and msdRNA, and stem-and-loop structures in RNA and DNA strands. However, it is encoded by a separate gene and is composed of a different nucleotide sequence (Dhundale et al., 1988b). A single copy chromosomal locus contains a gene, msd, which encodes the DNA strand of msDNA-Mx162 and a gene, msr, which encodes the RNA molecule. The two genes are convergently situated (5' to 3') such that their respective 3' ends overlap by 8 bases. In a clinical strain of *E. coli*, msDNA (msDNA-Ec67) which shares the same secondary structures but has a different primary sequence from the myxobacterial msDNAs, is also encoded by a single chromosomal locus. Situated about 50 bases from this locus is an open reading frame (ORF) which displays sequences comparable to known retroviral reverse transcriptases (RT) (Lampson et al., 1989). In Inouye et al., 1989, an ORF located 77 bases upstream of the msd gene of *M. xanthus* is described. Like that of *E. coli*, this ORF also shows significant amino acid sequence similarity to retroviral RT.

From S1 mapping experiments, the msdRNA of *M. xanthus* encoded by the msr gene is derived from a much longer precursor transcript which is likely to form a stable stem-and-loop structure (Dhundale et al., 1987). In addition, we proposed a model to explain the synthesis of the msDNA molecule in which the folded precursor RNA serves as both a primer and template for the synthesis of the branch-linked DNA strand via a reverse transcriptase activity. This application describes a cell-free system utilizing permeablized cells treated with phenethyl alcohol to study the biosynthesis of msDNA in *M. xanthus*. In this system [α-=p]dCPT is incorporated into msDNA. Intermediate structures were identified by interrupting the synthesis of msDNA with dideoxyribonucleotides. Analysis of the intermediate species provides compelling evidence that msDNA is synthesized from an RNA template by RT activity, and that there is a very precise coupling between RT activity and ribonuclease H (RNase H) activity.

BRIEF DESCRIPTION OF DRAWINGS

*M. xanthus* cells treated with phenethyl alcohol (PEA) were incubated for 10 min at 37° C. in a reaction mixture containing [α-$^{32}$P]dCTP. Total RNA was then extracted from the cells and the labeled species separated on a 4% acrylamide-8M urea gel. Gel lanes are: Lane S, radio-labeled pBR322 digested with MspI as molecular weight markers; lane 1, RNA from PEA treated cells incubated in the complete reaction mixture; lane 2, the same sample as in lane 1 after digestion with RNase A; lane 3, RNA obtained as above from the reaction mixture containing ddGTP; lane 4, the same sample as in lane 3 after digestion with RNase A; lane 5, purified msDNA obtained from *M. xanthus* (produced in vivo) treated with RNase A and 3' and labeled with terminal deoxynucleotidyl transferase; lane 6, RNA extracted from cells not treated with PEA prior to incubation with the complete reaction mixture; and lane 7, same sample as in lane 6 after digestion with RNase A. The numbers 160 and 240, with arrows indicate the approximate size of each band in nucleotide bases.

Permeablized cells were incubated in a reaction mixture for 2 min containing the DNA chain terminating analog ddGTP. RNA was extracted from the cells and electrophoresed on a 4% acrylamide-8M urea gel. A single radio-labeled band of 240 bases corresponding to msDNA (same as in lane 3, FIG. 1) was cut out of the gel and purified. the purified material was then applied to a 6% acrylamide-8M urea sequencing gel as shown. In each lane is: lane S, pBR322 molecular weight markers as in FIG. 1; lane 1, the 240 base, gel purified intermediate species of msDNA (arrow A) (note that the band migrates a bit slower in this gel system); land 2, the same purified material after RNase A digestion; lane 3, 3' end labeled msDNA (arrow B) (same as in lane 5, FIG. 1).

Permeablized cells were incubated in separate reaction mixtures containing either ddGTP, ddATP, ddTTP (instead of dGTP, dATP, dTTP in the complete reaction mxiture), or the complete reaction mixture. The intermediate species of msDNA produced from each reaction was purified as described in FIG. 2 and analyzed on a 6% acrylamide-8M urea sequencing gel. After RNase A digestion of each sample a "ladder" of different size DNA bands appears. From the pattern of bands, a partial DNA sequence was determined by reading the ladder like a standard dideoxy sequencing gel. The DNA sequence is shown on the right hand side of the gel and corresponds exactly to the known sequence of msDNA from position 75 to 110 (Dhundale et al., 1987). In each lane is: Lane S, molecular weight markers as in FIG. 2; lane 1, purified labeled band from a complete, in vitro reaction (same as in lane 1, FIG. 1); lane 2, the same sample as in lane 1 after RNase A treatment (the bands produced in lanes 1 and 2 were from a complete in vitro reaction in which no cold dCTP was added. Note that in addition to the full-size msDNA (arrow) there is a ladder of smaller molecular weights (lane 2). This ladder is formed at each C position because of the small concentration of [a-$^{32}$P]dCTP present. The faint bands that appear below the full length DNA allow the C positions in the DNA sequence to be determined); lane 3, purified band from a ddGTP, in vitro reaction after RNase A digestion; similarly lane 4, a ddATP reaction; lane 5, a ddTTP reaction. A dot is placed at each T position for the partial DNA sequence shown.

The $^{32}$P-labeled intermediate species produced from an in vitro reaction containing ddGTP was purified as described in FIG. 2. Samples treated or untreated with RNase H were electrophoresed on a 4% acrylamide-8M urea gel. Lane S contains molecular weight standards. Lane 1 contains the purified intermediate species before treatment with RNase H. Its size corresponds to about 240 nucleotide bases. Lane 2 contains the same sample as in lane 1 after treatment with RNase H. The resulting band is about 232 to 235 bases, having been reduced in size by 5 to 7 bases. Lane 3 contains purified msDNA (from M. xanthus in vivo) labeled at the 3' end by terminal deoxynucleotidyl transferase. Its size corresponds to 162 bases.

DESCRIPTION OF THE PREFERRED EMBODIMENTS

Cell-free System

Initial attempts to synthesize msDNA in vitro using various preparations of cell extracts have been unsuccessful. However, msDNA was successfully produced in a permeablized cell system in which M. xanthus cells are treated with either phenethyl alcohol (PEA) or toluene to render them permeable to radio-labeled nucleoside triphosphates. With such a cell-free system the availability of precursor nucleotides can be controlled during the synthesis of msDNA allowing some of the requirements for synthesis to be determined, and to identify possible intermediate structures formed during the production of msDNA.

Figure 1:
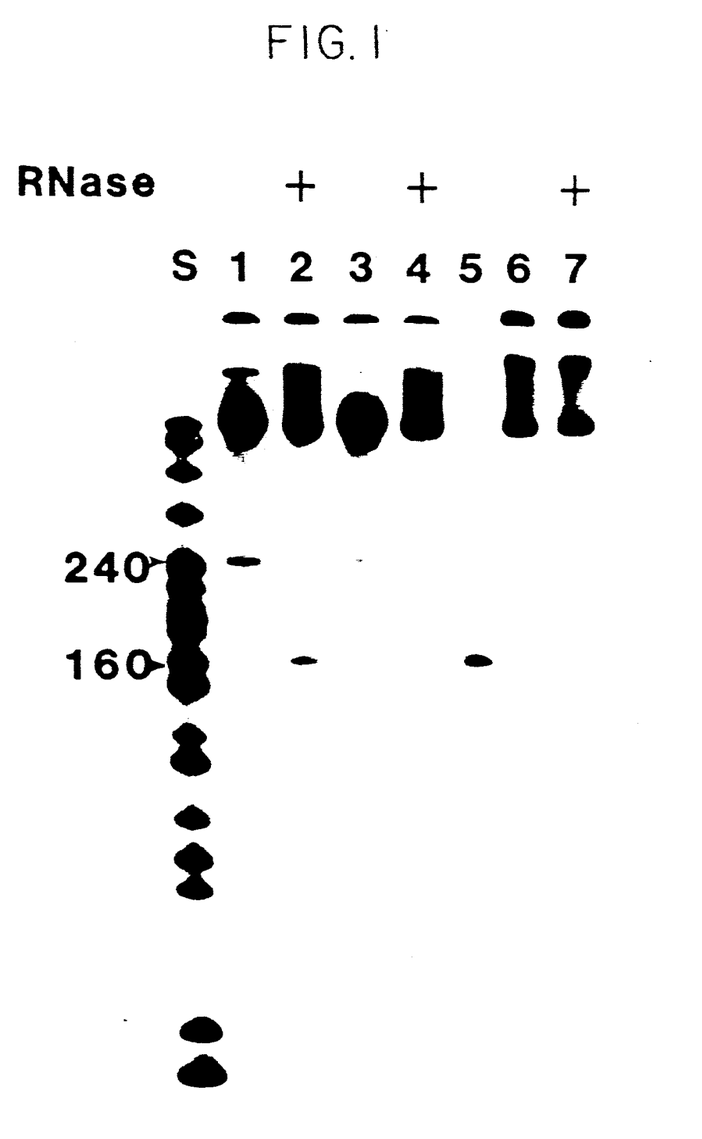
FIG. 1. Detection of msDNA Synthesized by the *M. xanthus* Cell-free System Utilizing Permeablized Cells.

FIG. 1 displays the results of a gel assay to detect the in vitro production of msDNA by permeablized cells. After gel electrophoresis of RNA prepared from PEA treated cells, two radio-labeled bands appear (lane 1). A large, high molecular weight band at the top of the gel appears to be chromosomal DNA which has incorporated radioactive nucleotide. This is probably due to repair type synthesis with DNA polymerase I, since the production of this band is not affected by nalidixic acid. A smaller, satelite band is also clearly discernable which migrates at about the equivalent molecular weight of 240 bases (lane 1, arrow). This is nearly identical to the expected size of the precursor form of msDNA from M. xanthus (the RNA-DNA complex of 239 bases). In order to confirm that this band is msDNA, the reaction sample was treated with RNase A prior to electrophoresis. This results in the appeerence of a new band of 160 bases, indicating that an RNA molecule of approximately 80 bases associated with the labeled DNA band has been removed by the RNase treatment. This is characteristic of msDNA, and the faster migrating band in lane 2 is nearly identical in size to the msDNA control in lane 5. the msDNA control contains purified msDNA after RNase treatment, which has been labeled at the 3' end of the DNA strand by terminal deoxynucleotidyl transferase. In addition, a deletion mutant strain of M. xanthus (Dhundale et al., 1988a) which can not produce msDNA was tested in an identical in vitro reaction. When RNA from PEA treated cells of the msd-msr deletion mutant is run on an electrophoresis gel no msDNA band is detected (not shown).

If the reaction sample is treated with DNase prior to electrophoresis, all the bands disappear causing a labeled smear running down the lane (not shown). If whole cells, not treated with PEA, are incubated in the reaction mixture and similarly processed, no detectable msDNA appears in the gel even after long exposure to film (lane 6 and 7). It is noted that some label becomes incorporated into the high molecular weight chromosome in untreated cells. This may be due to the incorporation of inorganic, radioactive phosphate generated by the hydrolysis of [a-$^{32}$P]dCTP.

Requirements for in vitro Synthesis msDNA synthesis is substantially reduced when dGTP is omitted from the complete system. Similar reductions are observed when other dNTPs are eliminated from the complete reaction mixture. Elimination of UTP, CTP or GTP showed a small reduction in msDNA synthesis. This is probably because there is enough existing pools of these nucleotides in the permeablized cells. The addition of nalidixic acid has no detectable effect on in vitro synthesis of msDNA. The addition of rifampicin has little effect on the production of msDNA. However, when the cell culture is exposed to rifampicin for 30 minutes just prior to PEA treatment, no detectable msDNA is produced. If the cell culture is exposed to nalidixic acid in the same way the level of msDNA produced is not affected.

These results indicate that the synthesis of msDNA is dependent on transcription by rifampicin-sensitive polymerase in vivo, while there seems to be no new initiation of msdRNA-precursor synthesis in the cell-free system. In contrast, nalidixic acid has no effect on msDNA synthesis both in vivo and in vitro. These features are similar to events previously observed from pulse-chase experiments during in vivo production of msDNA by myxobacteria (Furuichi et al. 1987b; Dhundale et al., 1987).

Disruption of msDNA Production with ddNTPs: Intermediate Structures

Figure 2:
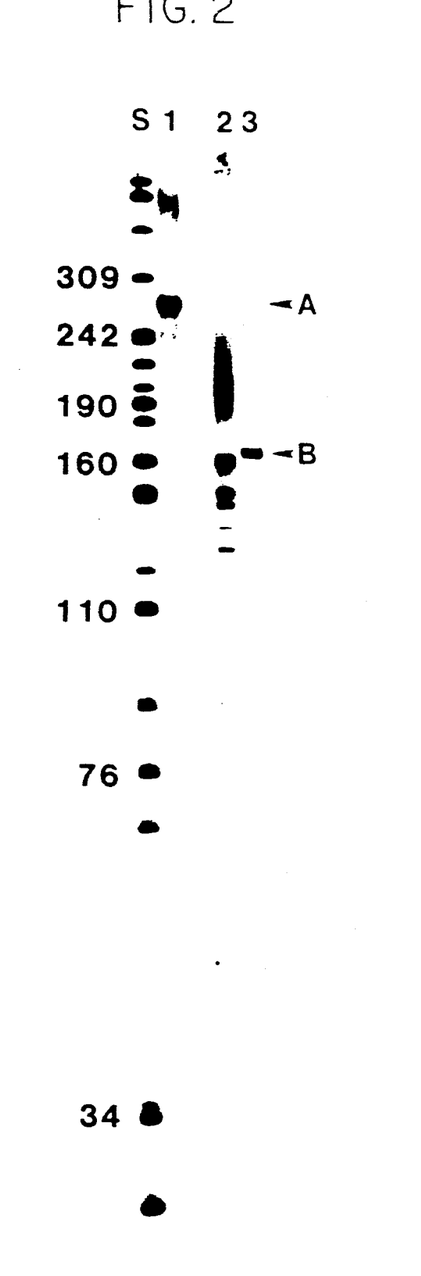
FIG. 2. Purified Intermediate Species of msDNA Synthesized in the *M. xanthus* Cell-free System.

In vitro synthesis of msDNA was interrupted by adding the chain terminating analog, dideoxy-GTP (ddGTP) to the reaction mixture. The resulting intermediate structures were detected on a gel and are shown in FIG. 1. In lane 3, total RNA prepared from permeablized cells incubated with ddGTP, reveals a single band identical in size to the precursor form of msDNA and indistinguishable from that seen in the complete reaction condition noted above (FIG. 1, lane 1). When the same RNA preparation is treated with RNase A, however, no band corresponding to the full length DNA strand of 162 bases is detectable. Instead a series of smaller bands appear. Although not visible in lane 4, longer exposure reveals a clear ladder such as shown in FIG. 2, lane 2. This ladder of DNA bands represents the intermediate lengths of DNA formed as a result of premature chain termination due to ddGTP incorporation during synthesis of msDNA.

Figure 3:
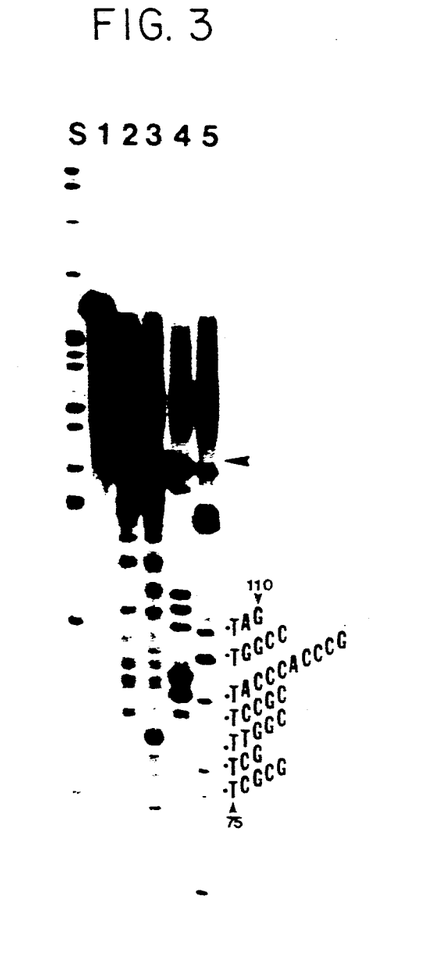
FIG. 3. Detection of Intermediates with DNAs of Various Lengths Produced in the Cell-free System.

In order to confirm that the single (240 bases) band observed prior to RNase treatment is the source of the ladder of DNA bands, this band was isolated and purified. After isolation and elution of the single msDNA band from an acrylamide gel, a portion of the purified species was treated with RNase A and then analyzed, along with an untreated sample, on a 6% acrylamide-sequencing gel. Lane 1 of FIG. 2, shows that the purified msDNA band, labeled in the complete reaction mixture with [$\alpha$-$^{32}$P]CTP in which dGTP was replaced with ddGTP, migrates as a single species of about 240-250 bases before digestion with RNase A. And as observed before, when the purified band is digested with RNase A, a series of small molecular weight bands appear like a sequencing ladder (lane 2). Other DNA sequencing ladders can be generated using ddATP and ddTTP. In this experiment permeablized cells were incubated in the complete reaction mixture supplemented with either ddGTP, ddATP, or ddTTP instead of dGTP, dATP or dTTP, respectively. The 240 base radio-labeled band (msDNA-RNA) observed in each reaction was purified from acrylamide gels. The purified material was treated with RNase A and separated on a sequencing gel. The pattern of bands observed in FIG. 3 lanes 3-5 is essentially the same as a Sanger-dideoxy sequencing ladder. Note that a sequencing ladder is obtained even without the addition of dideoxy analogs as shown in lane 2, FIG. 3. In this case the ladder is formed because of the limited availability of dCTP in the complete reaction mixture. It should also be noticed that in the G lane (lane 3) both the G ladder and the C ladder appear, while in the A lane (lane 4) and the T lane (lane 5) no apparent C ladder is detected. The reason for this disappearance of the C ladder in the A and T ladders is not clear at present. Using these ladders a part of the sequence can be determined. As shown in FIG. 3, the sequence determined by the gel is identical to the DNA sequence of msDNA from position 75 to 110. Above position 110 it is not easy to read the sequence because of the compression effect at various sites. Such compression effects are considered to be due to the stable secondary structures in msDNA. The sequence below position 75 is not discernible due to the poor incorporation of [$\alpha$-$^{32}$P]CTP.

Figure 4:
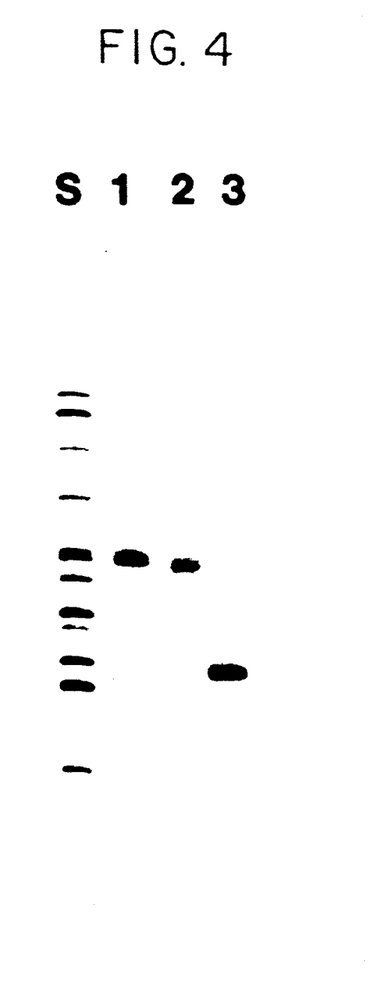
FIG. 4. Ribonuclease H-susceptibility of Intermediate Structures of msDNA Produced in vitro.

Analysis of the intermediate structures formed during the synthesis of msDNA, in vitro, clearly show that extension of the DNA strand has been interrupted by incorporation of dideoxy analogs or by a limited concentration of dCTP. This produces a ladder of small molecular weight DNA molecules. However, this series of intermediate length DNAs is only observed after treatment of the labeled species with RNase A, indicating that each molecule of DNA is associated with RNA of different sizes. It is also clear that prior to RNase A treatment, the $^{32}$P-labeled RNA-DNA complex that is produced during interrupted synthesis migrates as a single molecular weight species of 240 bases. We must conclude, therefore, that in order for the different sized DNAs to migrate as a single species they must be associated with different lengths of RNA such that each DNA-RNA complex is of the same total length of 240 nucleotides. In addition, the purified intermediate is susceptible to the action of RNase H (shown in FIG. 4). In this experiment, PEA treated cells were incubated with ddGTP as above. The 240 base intermediate structure was purified and then treated with RNase H, a nuclease which digests only RNA in a RNA-DNA duplex (Leis et al., 1973). Lane 1 of FIG. 4 shows the purified intermediate band prior to treatment and lane 2 after digestion with RNase H. Note the small shift in migration of the band after RNase H treatment indicating that each RNA-DNA complex contains a short RNA-DNA hybrid or duplex region. The size difference appears to be about 5 to 7 bases. When the same purified band (as in lane 1) is treated with RNase A, a ladder of small bands appear, identical to the ddGTP reaction in lane 2 of FIG. 2 (not shown). This result demonstrates that all the intermediates with different sized DNAs form RNA-DNA duplexes at their 3' ends.

Features of the intermediate structures observed during the in vitro production of msDNA are in agreement with the model previously proposed for the synthesis of msDNA in which the primary mRNA serves as a template for the synthesis of the DNA strand by reverse transcription. A description of the proposed mechanism for the synthesis of msDNA and how the observed intermediates have formed is discussed below.

Reverse Transcriptase Required for msDNA Synthesis

From evidence presented in the accompanying paper (Inouye et al., 1989), msDNA is associated with a gene for reverse transcriptase. In both the myxobacteria and E. coli (Lampson et al., 1989) the chromosomal gene encoding the DNA-RNA complex is closely linked to an ORF which codes for a protein having sequence similarity to retroviral RT. This ORF has been shown to be required for the production of msDNA in both M. xanthus and E. coli and to have demonstrated RT activity in E. coli. Data presented in here further supports the predicted requirement of RT for the synthesis of msDNA as proposed by Dhundale et al. (1987).

We have described an in vitro system to produce the branched RNA-linked msDNA molecule of M. xanthus. This system utilizes cells rendered permeable to the uptake and incorporation of labeled nucleoside triphosphates by treatment with PEA or toluene (Halegona et al., 1976). With this system, msDNA indistinguishable from that isolated in vivo was detected. In addition, intermediate structures were identified when synthesis of DNA was disrupted with ddNTPs. The intermediate species is composed of a complex of different sized DNAs, all smaller than the full length (162 bases) DNA found in the mature molecule, associated with a strand of RNA. Each DNA molecule is linked to a different length of RNA such that together, each RNA-DNA complex is composed of the same number of residues, i.e., 239 bases. Thus the purified intermediate species migrates as a single 239 base band, while after digestion with RNase A the intermediate appears as a ladder of various DNA bands. This intermediate structure, formed during the synthesis of msDNA, clearly demonstrates that the DNA strand is synthesized by reverse transcription from an RNA template associated with the complex. That is, as the DNA strand is extended along the RNA template, a corresponding length of RNA is digested away leaving a different sized RNA associated with each DNA in the intermediate structure. Such a concomitant ribonuclease activity associated with RT has not been demonstrated for retroviral RTs (Weiss et al., 1985). This is a clear demonstration that RNase H activity removes RNA from the 3' end, base by base, most likely in a concerted manner, as the DNA strand is extended by RT.

Mechanism for msDNA Synthesis

Figure 5:
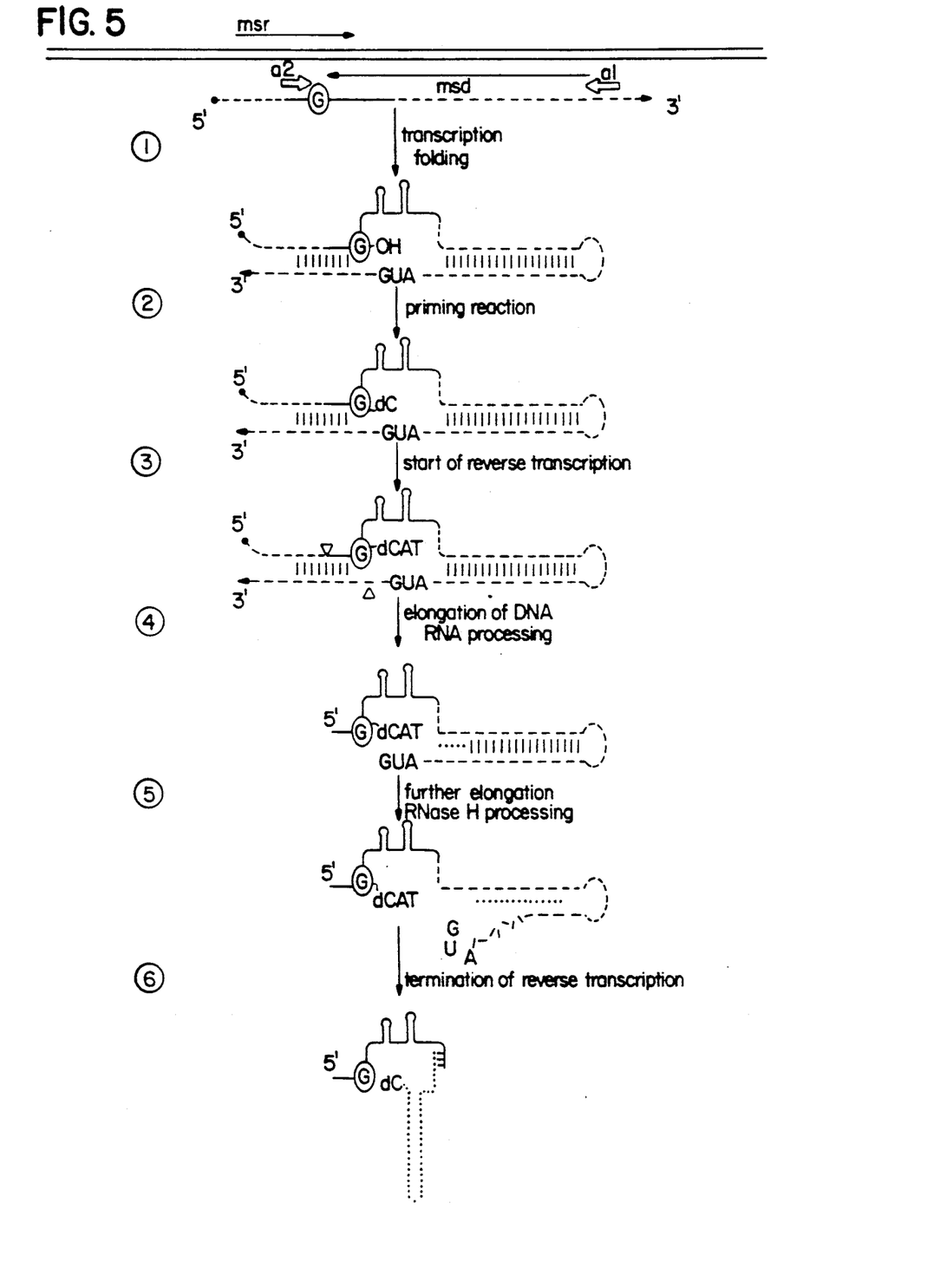
FIG. 5. Proposed Mechanism of Synthesis of msDNA from M. xanthus.

A model, previously proposed (Dhundale et al., 1987), predicts that such intermediate structures observed here will form during the synthesis of msDNA. The mechanism by which msDNA is formed is illustrated in FIG. 5: Synthesis of msDNA begins with transcription of a long RNA (step 1). From pulse-chase experiments (Furuichi et al., 1987b) as well as experiments presented here, rifampicin, which inhibits RNA polymerase, effectively blocks the synthesis of msDNA. S1 mapping analysis established that the primary transcript is about 375 bases long, beginning about 75 bases upstream of msr (the gene coding for RNA) and extending about 70 bases beyond the msd gene (encoding the DNA molecule). However, from studies of msDNA from *E. coli*, the primary transcript may be much longer, stretching beyond the msd gene and including the RT-ORF (see discussion in Inouye et al., 1989). Two inverted repeat sequences designated a1 and a2 (FIG. 5, step 1) allow the primary RNA molecule to fold into a stable stem-and-loop structure. This secondary structure positions the rG residue, which will contain the branched linkage in msDNA (circled in FIG. 5), in such a way as to be accessible for priming DNA synthesis. Correct positioning of the branched G in the folded RNA appears to be important for the synthesis of msDNA. Any mutation which disrupts the stem region immediately 5' to the branched G, blocks production of msDNA. It is worthy to note that the inverted repeats (a1 and a2) which correctly position the branched G are found in all msDNAs studied. Although their primary sequences are different, these inverted repeats are, in all cases, located immediately upstream of the branched G residue (a2) and immediately upstream of the start of the DNA coding region (a1).

After formation of secondary structure in the precursor RNA, a priming reaction (step 2) and initiation of reverse transcription (step 3) will follow the formation of the branched linkage between the 2'-OH of rG and the 5' end of the first deoxyribonucleotide. It is unclear, however, by what mechanism these events occur. It is not known whether the RT associated with msDNA is capable of initiating polymerization of DNA directly from the 2'-OH of rG. All known DNA polymerases require a 3'-OH primer (Weiss et al., 1985). It is possible that there is another enzyme which serves to prime the initiation of DNA synthesis. Alternatively, a non-enzymatic activation of the 2'-OH of the rG residue may be involved, which may include reactions similar to RNA selfsplicing, to produce a suitable primer.

Once elongation of DNA begins (step 4), after the priming and initiation reactions, there is an RNA processing event in which the first 75 bases from the 5' end and the last 70 bases from the 3' end of the RNA are removed. This produces the intermediate structure (the structure after step 4) observed in the cell-free system described in this paper. It is possible that this RNA processing may occur much earlier, for example during the priming reaction. As elongation of the DNA strand continues along the RNA template (by RT activity) there is a concomitant removal of the RNA template within the growing DNA-RNA duplex by RNase H activity (step 5). Like the RNase H associated with retroviral RTs, this RNase H activity may be an exonuclease requiring a free 3' end of RNA within the hybrid (Leis et al., 1973). Thus the RNA processing event (step 4) which removes (probably by an endonucleolytic cleavage) RNA from both the 5' end and especially the 3' end is considered to be an important step to initiate RNase H mediated digestion of the RNA template. This endonucleolytic scission may be similar to the removal of the tRNA primer by retrovirus RT (Omer and Faras, 1982). It is clear from analysis of the intermediate structures observed in this study that RNase H activity proceeds closely and in concert with polymerization of DNA by RT, to digest the RNA template in a 3' to 5' direction. In addition since the intermediate structures were found to retain a small five to seven base RNA-DNA hybrid (FIG. 4) this RNase H activity can be considered to be a partially processive exonuclease (Gerard, 1981). That is the enzyme remains bound to the substrate RNA chain as it proceeds with a series of digestions until it finally dissociates from the RNA before the RNA substrate is completely degraded leaving, in the case of msDNA-Mx162, an 8 base overlap in the RNA-DNA hybrid. The RT-RNase H enzyme complex terminates (step 6) at a distinct site about 16 bases before the stable stem-and-loop structure in the RNA molecule. This region of the RNA may serve as a termination signal for the RT reaction resulting in the dissociation of the complex from the template and completion of msDNA synthesis.

Production of msDNA in a cell-free system, described in this application, provides compelling evidence that msDNA is synthesized by a RT with an associated RNase H activity similar to retroviral RTs. However, from the amino acid sequence analysis of the ORF (Inouye et al., 1989) no recognizable RNase H domain is present in the *M. xanthus* RT. This is in contrast to the msDNA-RT from the *E. coli* clinical strain in which an RNase H domain appears in the carboxy terminal region of the protein similar to retroviral RTs (Lampson et al., 1989). It is possible that RNase H may still reside with the *M. xanthus* ORF, or RNase H may be encoded by a separate gene. In fact, other ORFs have been identified downstream of the RT gene, which may code for the RNase H protein.

Obtaining Permeablized Cells

Macromolecules such as deoxynucleoside triphosphates, normally do not penetrate the bacterial cell. However, after treatment of a cell suspension with toluene the cell is able to take up and incorporate a variety of chemical compounds. Early experiments showed that although cells treated with toluene are no longer viable they still retain the ability to repair and replicate DNA (Moses and Richardson, 1970), can synthesize certain RNA species (Peterson et al., 1971), and can synthesize membrane proteins (Halegona et al., 1976). Our permeablized cell system developed for *M. xanthus* is modified from previously published methods for *E. coli* from this laboratory (Halegona et al., 1976) and others (Moses and Richardson, 1970). Treatment of *M. xanthus* with either toluene or PEA was about equally effective in permeablizing cells to labeled nucleoside triphosphates (not shown). PEA is more soluble in water than toluene and thus was used for most experiments. In addition, from microscopic observation, most cells did not lyse after PEA treatment although their normal cell shape was altered.

Reaction Conditions

M. xanthus strain DZF1 is grown in CTT broth (Bretscher and Kaiser, 1978) to about mid logarithmic phase. The cells are washed in 50 mM phosphate buffer (pH 7.4) and then concentrated 5 fold. To one ml of concentrated cells ($2 \times 10^9$ cfu/ml) is added PEA to 0.5% and the cells are shaken very vigorously at room temperature for 2 min. Less than $10^2$ viable cfu/ml remain after 2 min. Treated cells are immediately added to a reaction mixture containing [$\alpha$-$^{32}$P]dCTP and incubated at 30° C. for 10 min. When ddNTPs are used, the corresponding dNTPs are omitted from the reaction mixture and the incubation is carried out at 30° C. for 2 min. The reaction mixture is composed of the following: $7 \times 10^6$ cfu of PEA treated cells; 70 mM phosphate buffer (pH 7.4); 13 mM MgCl$_2$; 1.3 mM ATP; 33 $\mu$M of each dGTP, dTTP, and dATP; 0.66 $\mu$M dCTP; 33 $\mu$M each rGTP, rUTP, and rCTP; and 0.02 $\mu$M [$\alpha$-$^{32}$P]dCTP. The cells are then pelleted and RNA is extracted by suspending the cells in a lysis solution containing 10 mM Tris-HCL (pH 8.0), 1 mM EDTA, 350 mM NaCl, 2% SDS, and 7M urea. This solution is then extracted with phenol:chloroform(1:1) followed by extraction with chloroform and ethanol precipitation. Synthesis of msDNA is assayed by electrophoresis of the RNA preparations on a 4% acrylamide-8M urea gel system or a 6% acrylamide-8M urea sequencing gel.

Nalidixic acid or rifampicin is added to a concentration of 50 $\mu$g per reaction volume, and ddNTPs are added to a final concentration of 2 $\mu$M. Intermediate structures were treated with RNase H, derived from E. coli (Boehringer Mannheim), for 30 min. at 37° C. in the recommended reaction buffer.

The expression vector, pUC9, contains a multiple cloning site located downstream of the lac Z gene. Insertions into the cloning site which are in frame with the lac Z structural gene result in the production of lac Z: foreign protein fusions. pUC9 is available from a number of commercial sources including Bethesda Research Laboratories, Gaithersburg, MD.

In accordance with the invention, it is contemplated that procaryotic reverse transcriptase, which is essential for msDNA synthesis, may be responsible for host cell parasitic or selfish DNA synthesis. Additionally, it is thought that the procaryotic reverse transcriptase molecule may be essential for synthesis of biological messengers and nucleic acid enzymes.

The msDNAs synthesized by the reverse transcriptase disclosed herein possess a highly stable RNA; it is capable of self-annealing and may serve as the primer for and as the template for msDNA synthesis. The reverse transcriptases (RTs) disclosed herein may be used as diagnostic agents. It is also contemplated that the RTs of the invention can synthesize msDNAs which will contain specific selected DNA fragments that can hybridize with complementary ssDNA, or otherwise identify ssDNAs, sought for, thus being useful as probes.

The possibility for the msDNAs to behave like restriction enzymes (or have enzyme restriction-like activity) in being capable of cleaving DNAs, or cut off a segment of itself, cannot be excluded.

REFERENCES

Bretscher, A. P., and Kaiser, D. (1978). Nutrition of Myxococcus xanthus, a fruiting myxobacterium. J. Bacteriol. 133, 763–768.

Dhundale, A., Furuichi, T., Inouye, M., and Inouye, S. (1988a). Mutations that affect the production of the branched RNA-linked msDNA in Myxococcus xanthus. J. Bacteriol. 170, 5620–5624.

Dhundale, A., Furuichi, T., Inouye, S., and Inouye, M. (1985). Distribution of multicopy single-stranded DNA among myxobacteria and related species. J. Bacteriol. 164, 914–917.

Dhundale, A., Inouye, M., and Inouye, S. (1988b). A new species of multicopy single-stranded DNA from Myxococcus xanthus with conserved structural features. J. Biol. Chem. 263, 9055–9058.

Dhundale, A., Lampson, B., Furuichi, T., Inouye, M., and Inouye, S. (1987). Structure of msDNA from Myxococcus xanthus: Evidence for a long, self-annealing RNA precursor for the covalently linked, branched RNA. Cell 51, 1105–1112.

Furuichi, T., Dhundale, A., Inouye, M., and Inouye, S. (1987a). Branched RNA covalently linked to the 5' end of a single-stranded DNA in Stigmatella aurantiaca: structure of msDNA. Cell 48, 47–53.

Furuichi, T., Inouye, S., and Inouye, M. (1987b). Biosynthesis and structure of stable branched RNA covalently linked to the 5' end of multicopy single-stranded DNA of Stigmatella aurantiaca. Cell 48, 55–62.

Gerard, G. F. (1981). Mechanism of action of Moloney Leukemia Virus RNA-directed DNA polymerase associated RNase H (RNase HI). Biochemistry 20, 256–265.

Halegona, S., Hirashima, A., Sekizawa, J., and Inouye, M. (1976). Protein synthesis in toluene-treated Escherichia coli. Eur. J. Biochem. 69, 163–167.

Inouye, S., Hsu, M.-Y., Eagle, S., and Inouye, M. (1988). Reverse transcriptase associated with the biosynthesis of the branched-RNA linked msDNA in Myxococcus xanthus. Cell 56, 709–717.

Kaiser, D. (1986). Control of multicellular development: Dictyostelium and Myxococcus. Ann. Rev. Genet. 20, 539–566.

Lampson, B. C., Sun, J., Hsu, M.-Y., Vallejo-Ramirez, J., Inouye, S., and Inouye, M. (1989). Reverse transcriptase in a clinical strain of E. coli: Its requirement for the production of branched RNA-linked msDNA. Science, 243, 1033–1038.

Leis, J. P., Berkower, I., and Hurwitz, J. (1973). Mechanism of action of ribonuclease H isolated from Avian Myeloblastosis Virus and Escherichia coli. Proc. Natl. Acad. Sci. U.S.A. 70, 466–470.

Moses, R. E., and Richardson, C. C. (1970). Replication and repair of DNA in cells of Escherichia coli treated with toluene. Proc. Natl. Acad. Sci. U.S.A. 67, 674–681.

Omer, C. A., and Faras, A. J. (1982) Mechanism of release of the Avian retrovirus tRNA$^{trp}$ primer molecule from viral DNA by ribonuclease H during reverse transcription. Cell 30, 797–805.

Peterson, R. L., Radcliffe, C. W., and Pace, N. R. (1971). Ribonucleic acid synthesis in bacteria treated with toluene. J. Bacteriol. 107, 585–588.

Shimkets, L. J. (1987). Control of morphogenesis in myxobacteria. Crit. Rev. Microbiol. 14, 195–227.

Weiss, N., Teich, H., Varmus, H., Coffin, J. Eds. (1985). RNA Tumor Viruses Vol. 2 (Cold Spring Harbor Laboratory, Cold Spring Harbor, N.Y.).

Yee, T., Furuichi, T., Inouye, S., and Inouye, M. (1984). Multicopy single-stranded DNA isolated from a gram-negative bacterium, *Myxococcus xanthus. Cell* 38, 203-209.

All of the above references are explicitly incorporated herein by reference.

We claim:

1. An in vitro method of synthesis for preparing a branched RNA-linked multi-copy single-stranded DNA (msDNA), having a 2',5'-phosphodiester linkage between the 5' end of the DNA and the branched RNA, comprising treating prokaryotic cells with a membrane-permeabilizing agent which renders the cells permeable to nucleoside triphosphates, incubating the permeabilized cells in a reaction mixture comprising substrates required for msDNA synthesis, and isolating the msDNA.

2. The process of claim 1 wherein the permeabilized cells are rendered non-viable by the treatment with the membrane-permeabilizing agent.

3. The method of claim 1 in which the reaction mixture comprises ATP, GTP, UTP, CTP, dATP, dGTP, dTTP and dCTP.

4. The method of claim 1 in which the prokaryotic cell is *Myxococcus xanthus.*

5. The process of claim 1 wherein the procaryotic permeabilized cell retains synthesis ability for RNA, DNA and protein.

6. The process of claim 1 wherein the membrane permeabilizing agent is an organic solvent selected from the group consisting of toluene and phenyl ethyl alcohol.

7. The process of claim 1 wherein the reaction mixture contains endogenous TTP, UTP, CTP and GTP.

8. The process of claim 7 which comprises the step of adding to the reaction mixture exogenous dTTP, dATP, dCTP and dGTP.

9. The process of claim 8 which comprises adding exogenous ATP.

10. The process of claim 9 wherein the added ATP is in excess of any one of the dTTP, dATP, dCTP and dGTP.

11. The process of claim 7 of synthesizing the msDNA which comprises the steps of synthesizing primary RNA molecule which folds into a stable stem-and-loop structure, thereby forming a secondary RNA structure, in which secondary RNA structure an rG residue is positioned to be accessible for priming DNA synthesis, priming and after formation of a branched linkage between the 2'-OH of rG and the 5' end of the first deoxyribonucleotide, synthesizing the DNA strand along the RNA template by reverse transcriptase, processing the RNA template by its RNase H mediated digestion, terminating the reverse transcriptase reaction by dissociation of the RT-RNase H enzyme complex from the template, completing the msDNA synthesis and isolating the msDNA.

12. The process of claim 11 wherein the processing of the RNA includes the removal of its first 75 bases from the 5' end and the last 70 bases from the 3' end.

13. The process of claim 11 wherein while synthesis of the DNA strand continues along the RNA template by reverse transcriptase, removal of the RNA template within the growing DNA-RNA duplex by the RNase activity takes place.

14. The process of claim 11 wherein the procaryotic cells are myxobacterium cells.

15. The process of claim 14 wherein the cells are *Myxococcus xanthus.*

16. The process of claim 11 wherein the primary RNA molecule contains two inverted repeat sequences which contribute to the folding into the stable-and-loop structure.

17. The process of claim 16 wherein the inverted repeats are positioned immediately upstream of the branched G residue and immediately upstream of the start of the DNA coding region.

* * * * *